United States Patent
Müller

(10) Patent No.: US 6,436,433 B1
(45) Date of Patent: Aug. 20, 2002

(54) TRANSDERMAL OR TOPICAL PLASTER SYSTEM WITH A POLYACRYLATE MATRIX WITH IMPROVED PHYSICAL PROPERTIES

(75) Inventor: Walter Müller, Neuwied (DE)

(73) Assignee: LTS Lohmann Therapie-Systeme AG, Andernach (DE)

(*) Notice: Subject to any disclaimer, the term of this patent is extended or adjusted under 35 U.S.C. 154(b) by 0 days.

(21) Appl. No.: 09/367,762
(22) PCT Filed: Feb. 9, 1998
(86) PCT No.: PCT/EP98/00685
§ 371 (c)(1), (2), (4) Date: Oct. 20, 1999
(87) PCT Pub. No.: WO98/36740
PCT Pub. Date: Aug. 27, 1998

(30) Foreign Application Priority Data

Feb. 21, 1997 (DE) .......................... 197 06 824

(51) Int. Cl.[7] .......................... A61F 13/02; A61F 13/00
(52) U.S. Cl. .................. 424/448; 424/449; 424/443
(58) Field of Search .................. 424/449, 448, 424/443

(56) References Cited

U.S. PATENT DOCUMENTS

| 4,882,163 A | * | 11/1989 | Guse et al. .................. 424/448 |
| 4,994,267 A | * | 2/1991 | Sablotsky .................. 424/78 |
| 5,089,267 A | * | 2/1992 | Hille et al. .................. 424/449 |
| 5,132,115 A | * | 7/1992 | Wolter et al. .................. 424/448 |
| 5,306,503 A | * | 4/1994 | Muller et al. .................. 424/449 |
| 5,834,010 A | * | 11/1998 | Quan et al. .................. 424/448 |

FOREIGN PATENT DOCUMENTS

| EP | WO 8600814 A | | 2/1986 |
| EP | WO 91/11978 | * | 8/1991 |
| EP | 0464573 A | | 1/1992 |
| EP | 0 856 311 | * | 12/1996 |
| EP | WO 96/40087 | * | 12/1996 |
| WO | WO 98 25591 A | | 6/1998 |

* cited by examiner

Primary Examiner—Thurman K. Page
Assistant Examiner—Isis Ghali
(74) Attorney, Agent, or Firm—D. Peter Hochberg; Katherine R. Vieyra; William H. Holt

(57) ABSTRACT

A transdermal or topical plaster system with a backing layer, with an active ingredient-containing and self-adhesive matrix based on crosslinkable polyacrylate as base polymer and with a removable protecting film is characterized by an at least two-layer matrix with a degree of crosslinking of the layer facing the skin which is appropriate for adequate adhesion to the skin thereof and is lower than the degree of crosslinking of the layer or layers on top thereof.

2 Claims, No Drawings

TRANSDERMAL OR TOPICAL PLASTER SYSTEM WITH A POLYACRYLATE MATRIX WITH IMPROVED PHYSICAL PROPERTIES

This application is a 371 of PCT/EP98/00685 Feb. 9, 1998.

The invention relates to a transdermal or topical plaster system with a backing layer, with an active ingredient-containing and self-adhesive matrix based on crosslinkable polyacrylate as base polymer and with a removable protecting film.

Transdermal therapeutic systems (TTS) have now gained a firm place in the therapy of some disorders because of the special advantages of this administration form for certain active ingredients. The plasters available on the market differ from one another in respect of their technical construction and of the active ingredients, auxiliaries and polymers employed.

In respect of technical construction, essentially two plaster systems dominate the market at present. These are the so-called reservoir systems and the so-called matrix systems. The reservoir systems typically consist of a bag which is filled with a liquid preparation of the active ingredient. One side of the bag consists of a membrane which is permeable at least for the active ingredient, and is normally provided with a suitable adhesive. In the matrix systems, the active ingredient is incorporated into a polymer formulation (matrix) which is preferably also self-adhesive. Thus matrix systems consist in the simplest case of a flexible sheet or textile fabric which form the backing layer of the plaster, of one or more active ingredient-containing, preferably self-adhesive matrix layers and of a protecting layer to be removed before use.

Matrix systems to a certain extent represent the second generation of transdermal systems and are the preferred aim of new developments. Compared with reservoir systems, they have the advantage of greater comfort of wearing and greater inherent safety because there is no need to worry about dose dumping due to leakage from the reservoir. Such matrix systems are also used as so-called topical systems, in which case the active ingredient preferentially displays its effect at the site of application, and systemic availability is not aimed at.

The preferred polymer class for formulating the matrix comprises polyacrylate adhesives because they have a good adhesive power on the skin, are hypoallergenic and are available in a wide variety of types with different properties in respect of their physical and chemical properties.

The development of self-adhesive matrix systems is impeded by the fact that it is necessary to incorporate into the adhesive both the active ingredient and all the other auxiliaries such as, for example, permeation enhancers, and thus the properties of the adhesive are frequently compromised. This affects in particular the cohesion of the adhesive, which is then manifested during storage thereof by so-called cold flow and by adhesive residues remaining on the application site when the plaster is removed from the skin.

Cold flow means in this connection that the adhesive matrix begins to flow like a very viscous liquid between the backing layer and protecting layer during storage, and eventually the adhesive is no longer completely covered by the backing layer. This may result, for example, in the plaster sticking to the primary packaging container, which usually consists of a bag made from heat-sealed packaging material laminate, and thus becoming unusable.

These problems become particularly evident when the concentration of plasticizing active ingredients and/or auxiliaries dissolved in the adhesive is more than 10 per cent by weight and the total weight of the matrix exceeds 50 $g/m^2$.

As means of suppressing this cold flow with polyacrylate adhesives, the patent application WO 86/00814 provides for crosslinking of the polymer in such a way that the plasticizing action of the ingredients is compensated by crosslinking. However, it must be remembered in this connection that the tack of the plaster decreases so greatly when there is too much crosslinking that the adhesion to the skin becomes inadequate. Moreover the production of a plaster which adheres well and has acceptable cold flow remains problematic.

The same applies to the solution proposed in the Patent DE 40 20 144, of adding a film-forming nonadhesive polymer to the matrix.

The solution to the problem of improving the cohesion of the matrix without reducing the adhesive power on the skin has now surprisingly been found by constructing the matrix out of at least two layers which have, in particular, the same polymer composition and the same concentration of dissolved ingredients, where the layer(s) facing away from the skin have a degree of crosslinking which is sufficient to prevent cold flow, and the layer facing the skin has a degree of crosslinking which guarantees sufficient adhesion to the skin.

Accordingly, the plaster system according to the invention of the type mentioned at the outset is essentially characterized by an at least two-layer matrix with a degree of crosslinking of the layer facing the skin which is appropriate for adequate adhesion to the skin thereof and is lower than the degree of crosslinking of the layer or layers on top thereof.

The coating weight of the skin contact layer is in this case preferably 10–30 $g/m^2$. With such a thickness, the cold flow of the layer is negligibly small, while the degree of crosslinking affords excellent adhesion to the skin.

Further particular features of the invention are evident from the claims and the following description.

The crosslinking of the matrix layers to different extents can be effected in a manner known per se, such as, for example, by
  adding metal chelates such as, for example, aluminium acetylacetonate or titanium acetylacetonate,
  chemical crosslinking with reactive reagents such as, for example, melamine,
  crosslinking by electron irradiation,
  irradiation with UV light in the case of adhesives with appropriate functional groups suitable for this purpose.

Particular benefits arise according to the invention from the recognition that two important parameters which are crucial for the performance of the TTS are virtually unaffected by the degree of crosslinking. These are
  a) the saturation solubility of all low molecular weight substances, and thus also of the active ingredient and
  b) the diffusion coefficient of low molecular weight substances,
    whereby the definitive elaboration of a specific plaster system experiences a considerable improvement.

The saturation solubility, and thus the thermodynamic activity, of the active ingredient at a given concentration is unaffected because, in general, only a very small portion of the functional groups on the polymer which are necessary for the crosslinking participates in the crosslinking reaction. Thus, the contribution of the functional groups to the polarity of the polymer and thus also to its dissolving power is thus substantially retained. The diffusion coefficient of low molecular weight compounds remains substantially unaffected by the degree of crosslinking, because only the microviscosity of the polymer in the immediate vicinity of the diffusing compound is of importance for the diffusion. However, this microviscosity is virtually unaffected, owing to the great length of the polymer molecules, at all degrees of crosslinking necessary in practice.

Thus, once the matrix formulation which is based on a self-adhesive polyacrylate capable of crosslinking and which permits delivery of an amount, which is adequate for practical use, of active ingredient through the skin has been found, it is then possible directly to provide a construction according to the invention of this matrix composed of several layers with different degrees of crosslinking while optimizing the thickness, cohesion and adhesive power, without thereby affecting the permeation performance of the system.

This denotes a significant simplification for the development of matrix systems. It is a simplification because problems with the adhesive power and the cohesion frequently only become evident when the first clinical tests and stability studies have already been carried out. Reformulation, necessary at this stage, of the matrix in respect of its composition has hitherto meant that the results of these clinical tests and the stability studies have been put in doubt. Optimization of the matrix in the sense of this invention means that the results of the clinical tests can be completely accepted and no additional stability risks need be expected. This is made clear by means of the table shown below comparing permeation data for a plaster according to the invention with a two-layer matrix and a conventional plaster.

EXAMPLES FOLLOW TO ILLUSTRATE THE INVENTION.

Example 1
Plastic with Scopolamine as Active Ingredient 12.5 g of oleyl alcohol and 12.5 g of scopolamine are added to 100 g of a polyacrylate adhesive solution (Durotak 326–1753) with a solids content of 50%, and the solution is homogenized by stirring.

13.6 g of a 4 per cent solution of aluminium acetylacetonate in ethyl acetate are added to 80 g of this solution, and the solution is homogenized by stirring. The resulting solution is adhesive composition A.

0.85 g of the 4% solution of aluminium acetylacetonate in ethyl acetate is added to 20 g of the active ingredient-containing adhesive solution, and the solutions are also homogenized by stirring. The resulting solution is adhesive composition B with a lower metal chelate concentration.

Adhesive composition A is spread with a knife on a siliconized polyester sheet in a thickness such that a coating weight of 80 g/m$^2$ results after removal of the solvents. The dried composition is laminated with a 25 $\mu$m thick polyester sheet.

Adhesive composition B is spread with a knife on a siliconized polyester sheet in a thickness such that a coating weight of 20 g/m$^2$ results after removal of the solvents.

The dried composition is laminated with the dried film described above after removal of the siliconized sheet. It is now possible to cut finished plasters out of the four-layer laminate produced in this way and consisting of the 25 $\mu$m-thick polyester sheet, two differently crosslinked matrix layers and a siliconized polyester sheet.

The plaster produced in this way was subjected to a permeation study using a 0.127 mm-thick silicone membrane as model membrane for human skin in order to show that a two-layer matrix system with differing degrees of crosslinking in the sense of this invention shows virtually no difference from a conventional one-layer matrix system (made only of adhesive composition A in a thickness of 100 g/m$^2$) in respect of the permeation rate for the incorporated active ingredient. The artificial membrane was chosen in place of skin because the variability of natural skin specimens makes it difficult to show small differences between different plaster formulations. Otherwise, the test was carried out with the Franz diffusion cells described in the literature and known to the skilled person. The results of this test are shown in the table below. The amount of active ingredient incorporated and the active ingredient concentration were the same in the two systems. However, the adhesive power, and thus also the adhesive power on the skin, is significantly improved for the two-layer system according to the invention.

|  | Permeated amount of scopolamine base [$\mu$g/cm$^2$] after | | | | | | | | |
| --- | --- | --- | --- | --- | --- | --- | --- | --- | --- |
|  | 0 h | 2 h | 4 h | 6 h | 8 h | 24 h | 30 h | 48 h | 72 h |
| One-layer plaster | 0 | 14.1 | 30.4 | 44.8 | 59.3 | 152.9 | 185.4 | 263.2 | 355.8 |
| Two-layer plaster | 0 | 17.5 | 33.8 | 46.0 | 61.0 | 150.0 | 181.7 | 258.7 | 356.8 |

Example 2
Plastic with Tiaprofenic Acid as Active Ingredient 6 g of oleic acid and 15 g of tiaprofenic acid are added to 100 g of a polyacrylate adhesive solution (Durotak 326-1051) with a solids content of 50%, and the solution is mechanically stirred until all the tiaprofenic acid has dissolved.

15 g of a 4 per cent solution of aluminium acetylacetonate in ethyl acetate are added to 80 g of this solution, and the solution is homogenized by stirring. The resulting solution is adhesive composition A.

2 g of the 4 per cent solution of aluminium acetylacetonate in ethyl acetate are added to 20 g of the active ingredient-containing adhesive solution, and the solution is also homogenized by stirring. The resulting solution is adhesive composition B.

Adhesive composition A is spread with a knife on a siliconized polyester sheet in a thickness such that a coating weight of 100 g/m$^2$ results after removal of the solvents. The dried composition is laminated with a transversely elastic viscose fabric. Adhesive composition B is spread with a knife on a siliconized polyester sheet in a thickness such that a coating weight of 25 g/m$^2$ results after removal of the solvents. The dried composition is laminated with the dried film described above after removal of the siliconized sheet. The finished plasters can now be cut out of the four-layer laminate produced in this way and consisting of the viscose fabric, two differently crosslinked matrix layers and a siliconized polyester sheet.

What is claimed is:
1. Transdermal or topical plaster system consisting of a backing layer, an active ingredient-containing and self-adhesive matrix, and a removable protective layer, said matrix consisting of at least two layers which each consist of the same polymer composition having a crosslinkable polyacrylate as base polymer, and the same concentration of dissolved ingredients, but no tackifying agent, wherein the skin facing layer of the matrix has a coating weight of 10–30 g/m$^2$, the crosslinking of which does not reduce the adhesion power to the skin thereof and is lower than the cold flow preventing degree of crosslinking of the layer or layers on top thereof.

2. The plaster system of claim 1 wherein the matrix has a total coating weight of at least 50 g/m².

* * * * *